US008895006B2

(12) United States Patent
Tumer et al.

(10) Patent No.: US 8,895,006 B2
(45) Date of Patent: Nov. 25, 2014

(54) RICIN RIBOSOME BINDING PROTEIN COMPOSITIONS AND METHODS OF USE THEREOF

(75) Inventors: Nilgun Tumer, Belle Mead, NJ (US); Xiao-Ping Li, Flemington, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/412,601

(22) Filed: Mar. 5, 2012

(65) Prior Publication Data
US 2012/0251542 A1   Oct. 4, 2012

Related U.S. Application Data (60) Provisional application No. 61/449,248, filed on Mar. 4, 2011.

(51) Int. Cl.
| | | |
|---|---|---|
| *A61K 39/00* | (2006.01) | |
| *A61K 39/112* | (2006.01) | |
| *C07K 14/25* | (2006.01) | |
| *G01N 33/577* | (2006.01) | |
| *A61K 39/395* | (2006.01) | |
| *A61P 31/04* | (2006.01) | |
| *A61P 37/04* | (2006.01) | |
| *A61K 39/108* | (2006.01) | |

(52) U.S. Cl.
CPC ............ *A61K 39/0283* (2013.01); *C07K 14/25* (2013.01); *G01N 2800/42* (2013.01); *G01N 2333/415* (2013.01); *G01N 2333/25* (2013.01); *G01N 2500/00* (2013.01); *A61K 39/0258* (2013.01); *A61K 2039/522* (2013.01)

USPC ..... 424/139.1; 530/377; 530/350; 424/185.1; 424/190.1

(58) Field of Classification Search
None
See application file for complete search history.

(56) References Cited

PUBLICATIONS

Bowie et al (Science, 1990, 257:1306-1310).*
Greenspan et al. (Nature Biotechnology 7: 936-937, 1999).*
Colman (Res. Immunology, Jan. 1994, vol. 145, pp. 33-36).*
Di, R., et al. "Identification of amino acids critical for the cytotoxicity of Shiga toxin 1 and 2 in *Saccharomyces cerevisiae*." Toxicon. Mar. 15, 2011;57(4):525-39. Epub Dec. 22, 2010.
Garcia-Ortega, L., et al. "Deletion of the NH2-terminal beta-hairpin of the ribotoxin alpha-sarcin produces a nontoxic but active ribonuclease." J Biol Chem. May 24, 2002;277(21):18632-9. Epub Mar. 15, 2002.
Li, X.P., et al. "Ribosome depurination is not sufficient for ricin-mediated cell death in *Saccharomyces cerevisiae*." Infect Immun. Jan. 2007;75(1):417-28. Epub Nov. 13, 2006.
Li, X.P., et al. "A two-step binding model proposed for the electrostatic interactions of ricin a chain with ribosomes." Biochemistry. May 12, 2009;48(18):3853-63.
Li, X.P., et al. "Pentameric organization of the ribosomal stalk accelerates recruitment of ricin a chain to the ribosome for depurination." J Biol Chem. Dec. 31, 2010;285(53):41463-71. Epub Oct. 25, 2010.

* cited by examiner

*Primary Examiner* — Robert A Zeman
(74) *Attorney, Agent, or Firm* — Kathleen D. Rigaut; Robert C. Netter, Jr.; Dann, Dorfman, Herrell & Skillman (57) ABSTRACT

Compositions and methods for treatment of toxin poisoning are disclosed.

9 Claims, 5 Drawing Sheets

Figure 5. Protein sequence comparisons of mature RTA, Stx1A1 and Stx2A1

```
              10         20         30         40         50
  1  IPPKQYPIINFTTAGATVQSYTNFIRAVRGRLTTGADVRHEIPVLPNRVG   mRTA
  1  ---KEF-TLDFSTAKTYVDSLNVIRSAIGTPLQTISSGGTSLLMIDSGSG   mStx1A1
  1  ---REF-TIDFSTQQSYVSSLNSIRTEISTPLEHISQGTTSVSVINHTPP   mStx2A1

60         70         80         90        100
 51  ---LPINQRFILVELSNHAELSVTLALDVTNAYVVGYRAGNSAYFFHPDN   mRTA
 47  DNLFAVDVRGIDPEEGRFNNLR--LIVERNNLYVTGFVNRTNNVFYR---   mStx1A1
 47  GSYFAVDIRGLDVYQARFDHLR--LIIEQNNLYVAGFVNTATNTFYR---   mStx2A1

110        120        130        140        150
 98  QEDARAITHLFTDVQNRYTFAFGGNYDRLEQLAGNLRENIELGNGPLEEA   mRTA
 92  ---FADFSHVTFPGTTAVTLSGDSSYTTLQRVAGISRTGMQINRHSLTTS   mStx1A1
 92  ---FSDFTHISVPGVTTVSMTTDSSYTTLQRVAALERSGMQISRHSLVSS   mStx2A1

160        170        180        190        200
148  ISALYYYSTGGTQLPTLARSFIICIQMISEAARFQYIEGEMRTRIRYNRR   mRTA
139  YLDLMSHS-GTSLTQSVARAMLRFVTVTAEALRFRQIQRGFRTLDDLSG    mStx1A1
139  YLALMEFS-GNYMTRDASRAVLRFVTVTAEALRFRQIQREFRQALSETAP   mStx2A1

210        220        230        240        250
198  --SAPDPSVITLENSWGRLSTAIQESNQGAPASPIQLQRRNGSKFSVYDV   mRTA
188  RSYVMTAEDVDLTLNWGRLSSVLPDYHG---QDSVRVGR-----ISFGST   mStx1A1
188  -VYTMTPGDVDLTLNWGRISNVLPEYRG---EDGVRVGR-----ISFNNI   mStx2A1

260        270
246  SILIPIIALMVYRCAPPPSSQF       mRTA
230  NAILGSVALILN-CHHHASRVAR      mStx1A1
229  SAILGTVAVILN-CHHQGARSVR      mStx2A1
```

RICIN RIBOSOME BINDING PROTEIN COMPOSITIONS AND METHODS OF USE THEREOF

This application claims priority to U.S. Provisional Application No. 61/449,248 filed Mar. 4, 2011, the entire contents being incorporated herein by reference as though set forth in full.

This invention was supported by funds from the National Institutes of Health, Grant No. 5R01AI072425. The United States government has rights in this invention.

FIELD OF THE INVENTION

This invention relates to the fields of toxin research and biodefense. More specifically, the invention provides potent vaccines useful for the treatment and prevention of toxin poisoning in subjects in need thereof.

BACKGROUND OF THE INVENTION

Several publications and patent documents are cited throughout the specification in order to describe the state of the art to which this invention pertains. Each of these citations is incorporated herein by reference as though set forth in full.

The plant toxins, ricin and abrin and the bacterial toxins, Shiga and Shiga-like toxins are type II ribosome inactivating proteins that inhibit protein synthesis by removing a highly conserved adenine from the a-sarcin/ricin loop (SRL) of the large rRNA. They consist of a catalytic A chain covalently joined by a disulfide bond to a cell binding B chain and are highly toxic to eukaryotic cells. Ricin naturally exists in the seeds of Ricinus communis (castor bean), a plant native to Asia, the Middle East and southern Europe.

In the castor bean, ricin A and B chains are encoded by a single gene, which is translated into a pre-proprotein of 576 amino acids. The ricin precursor consists of a 35 residue N-terminal extension, which contains the signal sequence. The mature RTA, which consists of 267 residues, is joined to the 262 residue mature RTB by a 12 residue linker peptide. The signal peptide directs the protein into the endoplasmic reticulum (ER) where pro-ricin is core glycosylated and disulfide bonds are formed within the protein. Four disulfide bonds form within the RTB sequence and the fifth one joins RTA with RTB in the ricin holotoxin.

The B-chain of ricin (RTB) is a lectin that binds galactose or N-acetylgalactosamine receptors on the surface of target cells and promotes subsequent endocytosis of the A-chain (RTA). After RTB binds to its receptor on the surface of animal cells, a portion of the endocytosed RTA reaches the Golgi complex. RTA is an N-glycosidase that depurinates ribosomes in the cytosol by removing a specific adenine (A4324 in rat 28S rRNA) from the highly conserved SRL in the large rRNA (7, 8). RTA undergoes retrograde transport from the Golgi to the endoplasmic reticulum (ER) and is thought to enter the cytosol from the ER.

The depurination of the SRL has been reported to interfere with the elongation factor 1 (eEF-1) dependent binding of amino acyl-tRNA to the ribosome, as well as the GTP-dependent binding of elongation factor 2 (eEF-2) and inhibit protein synthesis at the translocation step. There is evidence that ricin induces apoptosis in a wide variety of animal cells by mechanisms other than protein synthesis inhibition. Ricin-induced apoptosis in HeLa cells was associated with oxidative stress, glutathione depletion and activation of the caspase 3 cascade, followed by downstream events leading to apoptotic cell death.

Since ricin and many other AB-toxins are quite stable, one or a few molecules are sufficient to kill cells. RTA has been used in cancer therapy as the active moiety of immunotoxins selectively targeted to cancer cells. Due to its potent cytotoxicity and wide availability, ricin has been exploited as a biological weapon and an agent of bioterrorism and has been classified as a level B biothreat by the Centers for Disease Control and Prevention. Inhalation of small amounts of ricin aerosol can rapidly and irreversibly damage cells of the respiratory tract, leading to severe pulmonary incapacitation or death.

SUMMARY OF THE INVENTION

Some aspects of the present invention are directed to non-toxic ricin and shiga like ribosome binding mutants. In some embodiments, the ricin mutant contains at least two alterations relative to a mature ricin A chain toxin of SEQ ID NO: 1 selected from the group consisting of i) R189A and R234A; ii) R193A and R235A; iii) R193A and R235A and R189A; iv) R193A and R235A and R234A; v) R193A and R235A and R189A and R234A; and vi) R213A and R258A.

In another embodiment, ribosome binding mutants of Stx1A1 toxin which are altered relative to the wild type sequence of SEQ ID NO: 2 are provided. Exemplary mutants are selected from the group consisting of i) R172A and R176A and R179A; ii) R205A and R220A; iii) R223A and R248A; and iv) R251A.

In yet another embodiment of the invention, ribosome binding mutants of Stx2A1 toxin which are altered relative to the wild-type sequence of SEQ ID NO: 3 are provided. Exemplary mutants are selected from the group consisting of i) R172A and R176A and R179A; ii) R204A and R219A; iii) R222A and R247A; and iv) R250A.

Nucleic acid molecules encoding the ricin, Stx1A1 and Stx2A1 mutants, and various constructs and cells, tissue or organisms containing same (e.g., transformed plants including edible plants) and methods of making the toxin mutants are also provided.

Other aspects of the present invention are directed to compositions containing the toxin mutant or the nucleic acid, and a carrier, and methods of using the mutants or nucleic acids, or compositions containing them.

Cell damage, particularly endothelial cell (EC) damage, produced by toxins such as ricin A chain for example, is a danger for individuals who have contact with such toxins. Individuals that are in danger of such contact include members of the armed services, as well as civilians, who may be exposed to chemical weapons or terrorist devices. Thus, in some embodiments, the compositions are in the form of a vaccine, wherein the toxin mutant (or the nucleic acid) is present (or in the case of the nucleic acid, is expressed) in an amount effective to elicit an immune response to the particular targeted toxin in an animal such as a human. Thus, a related aspect of the present invention is directed to a method of eliciting an immune response to a toxin, comprising contacting an animal with a mutant toxin as disclosed herein (or nucleic acid encoding the mutant toxin of the present invention in an amount effective to elicit an immune response to toxin, wherein an immune response to toxin is elicited in the animal, e.g., human. Due to their nontoxic (e.g., disarmed or attentuated) properties, the mutants of the present invention should elicit an effective immune response.

BRIEF DESCRIPTION OF THE DRAWINGS

FIG. 5. Comparison of the amino acid sequences of the mature form of wild type ricin A chain (mRTA; SEQ ID NO: 1), mature form of wild-type Stx1A1 chain (mStx1A1; SEQ ID NO: 2) and mature form of wild-type Stx2A1 chain (mStx2Al; SEQ ID NO: 3). Mature forms are missing the signal sequence.

DETAILED DESCRIPTION OF THE INVENTION

The ricin or shiga mutants of the present invention may be prepared by alteration of the encoding wild-type toxin DNA; taking into consideration also that the genetic code is degenerate and that two or more codons may code for the same amino acid. Nucleic acids encoding these immunogenic compositions also can be constructed and inserted into one or more expression vectors by standard methods (Sambrook, et al., In: Molecular Cloning: A Laboratory Manual, Vol. 1, Cold Spring Harbor Laboratory Press, Cold Spring Harbor, N.Y. 1989), for example, using PCR® cloning methodology.

For compositions containing the ricin or shiga mutants to be useful as a vaccine, wherein the toxin mutants function as an immunogen, an immune response to the immunogen must be produced in at least one cell, tissue or animal (e.g., a human). Thus, the present invention provides vaccine or immunogenic compositions that contain the mutant toxin (e.g., ricin or shiga) as the immunogen, a nucleic acid encoding the immunogen (e.g., an immunogen expression vector), or at least one cell expressing or presenting an immunogen. Vaccination via the compositions containing the ricin mutant encoding nucleic acid is generally achieved by transfecting or inoculating an animal with the nucleic acid, such that upon contact, animal target cells express the nucleic acid. Expression in vivo by the nucleic acid may be, for example, by a plasmid type vector, a viral vector, or a viral/plasmid construct vector.

In order to effect replication, expression or mutagenesis of a nucleic acid, the nucleic acid may be delivered ("transfected") into at least one cell. The transfection of cells may be used, in certain embodiments, to recombinantly produce one or more vaccine components for subsequent purification and preparation into a pharmaceutical vaccine. In other embodiments, the nucleic acid may be comprised as a genetic vaccine that is administered to an animal. In other embodiments, the nucleic acid is transfected into at least one cell and the cell administered to an animal as a cellular vaccine component.

The nucleic acids encoding the mutant, non-toxic mutants may be introduced into cells or organisms via a vector, which is generally regarded as a carrier nucleic acid molecule into which a nucleic acid sequence can be inserted for introduction into at least one cell where it can be replicated. The toxin mutant may be situated in the vector so as to be in operable association with one or more regulatory or other genetic elements, including promoters and enhancers that effectively directs the expression of the DNA segment in the organelle, cell type, tissue, organ, or organism chosen for expression, initiation signals and internal ribosome binding sites, multiple cloning sites, splicing sites, termination signals, polyadenylation signals, origins of replication, and selectable markers.

A variety of vectors may be useful in connection with the present invention, including plasmid vectors, viral vectors (e.g., adenoviral vectors, AAV vectors, AAV vectors, retroviral vectors (lentiviruses including HIV-1, HIV-2 and SIV), as well as viral vectors derived from vaccinia virus, sindbis virus, cytomegalovirus, and herpes simplex virus. The vectors may be targeted to specific target cells by means of a specific binding ligand.

Vectors containing the toxin mutant nucleic acids of the present invention may be delivered to organelles, cells, tissues or organisms to achieve administration of the genetic vaccine using known techniques. Representative techniques include direct delivery of DNA such as by injection, electroporation, calcium phosphate precipitation, DEAE-dextran followed by polyethylene glycol, direct sonic loading, liposome mediated transfection, receptor-mediated transfection, microprojectile bombardment, agitation with silicon carbide fibers, *Agrobacterium*-mediated transformation, PEG-mediated transformation of protoplasts and desiccation/inhibition-mediated DNA uptake. The targets may be stably or transiently transformed.

Representative host cells include prokaryotes and eucaryotes alike, including bacteria, viruses, yeast, plant cells and animal cells. As used herein, the terms "cell," "cell line," and "cell culture" may be used interchangeably. All of these terms also include their progeny, which is any and all subsequent generations, which may or may not be identical on account of deliberate or inadvertent mutations. A tissue may comprise a host cell or cells to be transformed with a nucleic acid encoding a vaccine component. The tissue may be part or separated from an organism, and may include adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, small intestine, spleen, stem cells, stomach, testes, anthers, ascite tissue, cobs, ears, flowers, husks, kernels, leaves, meristematic cells, pollen, root tips, roots, silk and, stalks.

In certain embodiments, the host cell or tissue may be comprised in at least one organism. In certain embodiments, the organism may be, but is not limited to, a prokayote (e.g., a eubacteria, an archaea) or a eucaryote, such as a plant, as would be understood by one of ordinary skill in the art. In some embodiments, a nucleic acid encoding a ricin mutant of the present invention is transformed and expressed in plants, particularly edible plants such as tomato, cucumber and banana. All or a part of the plant material may be used to prepare a vaccine, such as an oral vaccine. Such methods are described in U.S. Pat. Nos. 5,484,719; 5,612,487; 5,914,123; and 5,977,438.

The compositions may also contain at least one additional immunostimulatory agent or nucleic acids encoding such agents separately or as a fusion. Examples of such agents include additional immunogens, immunomodulators, antigen presenting cells and adjuvants. One or more of the additional agents may be covalently bonded to the antigen or an immunostimulatory agent. The immunogenic composition may be conjugated to or contain an HLA anchor motif amino acids.

The vaccine compositions of the present invention may vary in a few ways, including the active component (which may be present in neutral form or in the form of a pharmaceutically acceptable base or salt) and the manner in which it is packaged for contact with cells of the animal e.g., administration or delivery. For example, a nucleic acid encoding the toxin mutant may be formulated with an adjuvant that is a protein. The immunogen or nucleic acid may be encapsulated in a lipid or liposome. Even further, it may be in the form of a cellular vaccine wherein the cell has been transformed with the toxin mutant encoding nucleic acid. Such cellular hosts may be in culture, tissue, organ or an organism. They are isolated and then contacted with the cells of the animal.

Immunomodulators may augment the immune response. A variety of immunomodulators are known in the art. They include cytokines (e.g., interleukin 1 (IL-1), IL-2, IL-3, IL-4, IL-5, IL-6, IL-7, IL-8, IL-9, IL-10, IL-11, IL-12, IL-13, IL-14, IL-15, IL-18, beta-interferon, alpha-interferon, gamma-interferon, angiostatin, thrombospondin, endostatin, GM-CSF, G-CSF, M-CSF, METH-1, METH-2, tumor necrosis factor, TGF-beta and LT); chemokines (e.g., RANTES, MCAF, MIP1-alpha, MIP1-beta and IP-10); immunogenic carrier proteins (e.g., hepatitis B surface antigen, keyhole limpet hemocyanin (KLH) and albumins e.g., bovine serum albumin (BSA), ovalbumin, mouse serum albumin and rabbit serum albumin); biological response modifiers (e.g., cimetidine (CIM; 1200 mg/d) (Smith/Kline, Pa.); low-dose cyclophosphamide (CYP; 300 mg/M.sup.2) (Johnson/Mead, N.J.), or a gene encoding a protein involved in one or more immune helper functions, such as B-7); and adjuvants (e.g., alum, used in about 0.05 to about 0.1% solution in phosphate buffered saline; synthetic polymers of sugars (Carbopol®)) used as an about 0.25% solution; aggregation of the immunogen e.g., with heat, pepsin-treated (Fab) antibodies to albumin, mixture with bacterial cell(s) such as C. parvum or an endotoxin or lipopolysaccharide components of Gram-negative bacteria, emulsion in physiologically acceptable oil vehicles, such as mannide mono-oleate (Aracel A) or emulsion with a 20% solution of a perfluorocarbon (Fluosol-DA®) used as a block substitute, muramyl dipeptide (N-acetylmuramyl-L-alanyl-D-isoglutamine [MDP]), polysaccharides and polyamine varieties of polysaccharides such as chitin and chitosan, BCG (bacillus Calmette-Guerin, an attenuated strain of Mycobacterium), BCG-cell wall skeleton (CWS), with or without trehalose dimycolate; amphipathic and surface active agents, e.g., saponin and derivatives such as QS21 (Cambridge Biotech); nonionic block copolymer surfactants; oligonucleotides; Quil A; lentinen; and detoxified endotoxins. In embodiments wherein the toxin mutant nucleic acid is contained in a cell, the adjuvant may be incorporated into or otherwise physically associated with or conjugated to the cell membrane.

The vaccine compositions of the present invention (or individual components thereof) may be purified to the degree desired or necessary, given the particular circumstances and/or the hosts to which it is administered. Purification of the toxin mutants of the present invention or the nucleic acids can be carried out in accordance with standard techniques. Protein purification techniques include precipitation with ammonium sulfate, PEG or antibodies, or by heat denaturation, followed by centrifugation; fractionation; chromatographic procedures e.g., partition chromatograph (e.g., paper chromatograph, thin-layer chromatograph (TLC), gas-liquid chromatography and gel chromatography), gas chromatography, high performance liquid chromatography, affinity chromatography, supercritical flow chromatography, ion exchange chromatography, gel filtration chromatography, reverse phase chromatography, hydroxylapatite chromatography, lectin affinity chromatography; isoelectric focusing and gel electrophoresis. The toxin mutant encoding nucleic acids may be purified on polyacrylamide gels or cesium chloride centrifugation gradients. Cells or other components of the vaccine may be purified by flow cytometry.

Vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art. The quantity to be administered depends on the subject to be treated, including, e.g., the capacity of the individual's immune system to mount an immune response, and the degree of protection desired. The dosage of the vaccine will depend on the route of administration and will vary according to the size of the subject. Precise amounts of an active ingredient required to be administered depend on the judgment of the practitioner. Dosage amounts of the ricin mutants generally range from about 1 µg to about 250 µg or more, and in some embodiments from about 1 to 100 µg, or even about 10 to about 50 µg, or any range derivable therein.

Advantageously, the vaccines are administered to animals, e.g., humans prior to exposure or contact (confirmed or suspected) to ricin or shiga toxin. However, administration may follow such exposure or contact.

Suitable regimes for initial administration and subsequent booster administrations may vary. Typically, an initial administration is followed by at least one booster. To achieve acceptable immunity, multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals, e.g., monthly. See, e.g., Vitetta, et al., PNAS 103(7):2268-73 (2006). Periodic boosters at intervals of 1-5 years, usually three years, will be desirable to maintain protective levels of the antibodies to the ricin mutants.

The following definitions are provided to facilitate an understanding of the present invention.

A. DEFINITIONS

As used herein, "protein synthesis inactivating toxin" includes toxins that are ribonucleases, N-glycosidases, or ADP-ribosyltransferases. N-glycosidases are exemplified by the single polypeptide of the plant type I ribosome inactivating proteins (RIP) (e.g., gelonin, momordin, and saporin), the "A" chain of the plant type II ribosome-inactivating proteins (e.g., ricin, abrin, and modeccin), and similar acting bacterial toxins (e.g., Shiga toxins). The term "protein synthesis inactivating toxin" as used herein also includes specific ribonucleases that digest a specific phosphodiester bond in the backbone of ribosomal RNA, thereby inactivating the ribosomes and inhibiting protein synthesis. Ribonucleases are exemplified by the fungal toxins alpha-sarcin, mitogillin, and restrictocin, and also include similar acting bacterial toxins.

The term "protein synthesis inactivating toxin" also includes the ADP-ribosylating component of the ADP-ribosyltransferases, which are proteolytically activated bacterial toxins that ADP-ribosylate, and thus inactivate, components of the protein synthesis machinery (e.g., diphtheria toxin and Pseudomonas exotoxin A).

Plant ribosome-inactivating proteins (RIPs) are N-glycosidases that cleave (i.e. depurinate) the N-glycosidic bond of adenine in a specific ribosomal RNA sequence. Many RIPs are single-chain proteins (type I RIPs), but some (type II RIPs) possess a galactose-specific lectin domain that binds to cell surfaces. The type II RIPs are potent toxins, and include, for example, ricin.

As used herein, "type II ribosome-inactivating proteins" or "type II RIPs" means two-chain N-glycosidases that cleave the N-glycosidic bond of adenine in a specific ribosomal RNA sequence, wherein the two chains are an A chain, which possesses the N-glycosidase activity, and a B chain, which comprises a galactose-specific lectin domain that binds to cell surfaces. Ricin is one example of a prototypical type II ribosome-inactivating protein, but other such type II RIPs include abrin (from *Abrus precatrius*), modeccin (from *Adenia digtata*), viscumin (from *Viscum album*), Shiga toxin (from *S. dysenteriae*), and volkensin (from *Adenia volkensii*).

As used herein, "ricin A chain" of "RTA" means an N-glycosidase of about 32 KDa that digests and inactivates 26S and 28S ribosomal RNA by cleavage of a specific adenine residue located within a highly conserved region of the 26S and 28S ribosomal RNA. The RTA sequence is known in the art and is disclosed in US Patent application 2010/0285046.

As used herein, "ricin B chain" or "RTB" means a galactose/N-acetylgalactosamine-binding lectin of about 34 KDa.

By "wild-type Stx2A," it is meant the mature Stx2 A subunit amino acid sequence 1-297, excluding the 22-amino acid N-terminal signal peptide ("the N-terminal signal sequence of wild-type Stx2"). Thus, by the term "wild-type Stx2A", or "Stx2A", it is meant the Stx2 amino acid sequence 1-297 (hereinafter Stx2 (1-297)). These sequences are known in the art and are disclosed in US Patent Application 2010/0298238.

By the term "nontoxic", it is meant that the mutants are less toxic to yeast cells than wild-type Stx1 or wild-type Stx2, i.e., they do not significantly inhibit cell growth (like wild-type Stx1 or Stx2) and they do not significantly affect cell viability. This determination can be made in accordance with a combination of standard techniques, illustrations of which are set forth in commonly owned United States Patent Application Publication 2004/0241673, which is hereby incorporated herein by reference, as well as in the working examples below.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula $C=C(OR)$ where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula $C=C(OC(O)R)$ where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, "treatment" means any manner in which one or more of the symptoms of a protein synthesis inactivating toxin poisoning, e.g., ricin, abrin, a Shiga toxin, or a Shiga-like (e.g., *E. coli* 0157:57) toxin poisoning, are ameliorated or otherwise beneficially altered. Treatment also encompasses any pharmaceutical use of the compositions herein, such as uses for treating diseases, disorders, or ailments in which a protein synthesis inactivating toxin is implicated.

As used herein, "amelioration" of the symptoms of a particular disorder by administration of a particular compound or pharmaceutical composition refers to any lessening, whether permanent or temporary, lasting or transient that can be attributed to or associated with administration of the composition.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

B. INJECTABLES, SOLUTIONS, AND EMULSIONS

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration should be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

C. LYOPHILIZED POWDERS

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

D. TOPICAL ADMINISTRATION

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 20 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

E. COMPOSITIONS FOR OTHER ROUTES OF ADMINISTRATION

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

F. ARTICLES OF MANUFACTURE

The compounds or pharmaceutically acceptable derivatives may be packaged as articles of manufacture (e.g., kits) containing packaging material, a compound or pharmaceutically acceptable salt or derivative thereof provided herein within the packaging material, and a label that indicates that the compound or composition, or pharmaceutically acceptable derivative thereof, is useful for treatment, prevention, or amelioration of one or more symptoms or disorders in which a protein synthesis inactivating toxin poisoning, including ricin, abrin, a Shiga toxin, or a Shiga-like toxin poisoning, is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

G. SUSTAINED RELEASE FORMULATIONS

Also provided are sustained release formulations to deliver the compounds to the desired target at high circulating levels (between $10^{-9}$ and $10^{-4}$ M). The levels are either circulating in the patient systemically, or in one embodiment, localized to a site of, e.g., paralysis.

It is understood that the compound levels are maintained over a certain period of time as is desired and can be easily determined by one skilled in the art. Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions provided herein. Thus, single unit dosage forms suitable for oral administration, such as, but not limited to, tablets, capsules, gelcaps, caplets, powders and the like, that are adapted for sustained release are contemplated herein.

Preparations for oral administration may be suitably formulated to give controlled release of the active compound. In one embodiment, the compounds are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compositions provided herein may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

Methods of Use of the Compositions of the Invention

Provided herein are methods to treat, prevent, or ameliorate symptoms or disorders associated with a protein synthesis inactivating toxin poisoning, including ricin, abrin, a Shiga toxin, or a Shiga-like toxin poisoning. The methods include administering one or more of the compounds described herein, or a pharmaceutically acceptable salt form or derivative thereof, to a mammal, e.g., a human, cat, dog, horse, pig, cow, sheep, mouse, rat, or monkey.

In certain embodiments, the symptoms or disorders associated with a protein synthesis inactivating toxin may depend on the route of exposure. In some embodiments, exposure to a protein synthesis inactivating toxin may occur via inhalation, ingestion, or injection. In some embodiments, the symptoms or disorders associated with a protein synthesis inactivating toxin poisoning may depend on the dose received. In some embodiments, the symptoms or disorders associated with a protein synthesis inactivating toxin poisoning include one or more of respiratory distress (difficulty breathing), fever, cough, nausea, tightness in the chest, heavy sweating, fluid build-up in the lungs (pulmonary edema), low blood pressure, respiratory failure, vomiting, diarrhea, severe dehydration, hallucinations, seizures, blood in the urine, liver failure, spleen failure, and kidney failure.

In practicing the methods, effective amounts of the compositions provided herein are administered. Such amounts are sufficient to achieve a therapeutically effective concentration of the compound or active component of the composition in vivo.

Example I

Identification of Amino Acids that Differentially Affect Ribosome Binding and Catalytic Activity of Ribosome Inactivating Proteins It is known that the basic amino acids located at the interface between the A and the B subunits of ricin and Shiga toxins are involved in ribosome and ribosomal RNA (rRNA) binding. Previous studies have revealed that that single mutations at these residues are not sufficient to reduce toxicity. Multiple mutations are needed are needed for this purpose. In order to identify mutants that would exhibit the desired reduced cytotoxicity, we utilized site directed mutagenesis of ribosome binding residues, and then compared the depurination activity of the mutants using intact ribosomes and naked rRNA as substrates. These studies revealed a series of ribosome/rRNA binding mutants exhibiting significantly reduced cytotoxicity which have utility in vaccine development against ricin (and Shigella or Shiga toxin-producing E. coli STEC) intoxication.

In another approach, these ribosome binding mutants can be used in epitope mapping studies to identify epitopes where neutralizing antibodies bind to the toxin. Moreover, since this region is conserved between different RIPs, similar sequences may be critical for ribosome binding of other ribosome inactivating proteins (RIPs). In this approach, monoclonal antibodies made against ricin would be screened to identify those that bind to the ribosome binding sequences shown in Table 1 (Arg189, Arg234, etc). Such antibodies, when passively infused into patients, (e.g., passive immunotherapy) can bind to the ribosome binding sequences of ricin and prevent its binding to the ribosome and therefore neutralize the toxicity of ricin.

Although some structural motifs have been implicated in the interaction of ribotoxins with the SRL (3, 4), the residues that contribute to recognition of the ribosome target by ribosome inactivating proteins (RIPs) such as ricin and Shiga toxins have not been identified. We have identified amino acids critical for ribosome binding of ricin A chain (RTA) and showed that mutation of these residues affects the activity of toxin on ribosomes, its translation inhibitory activity and cytotoxicity in mammalian cells. These RTA mutants are potentially excellent vaccine candidates. They can also be used in epitope mapping studies to identify the binding sites of potential vaccine candidates.

Figure 1:
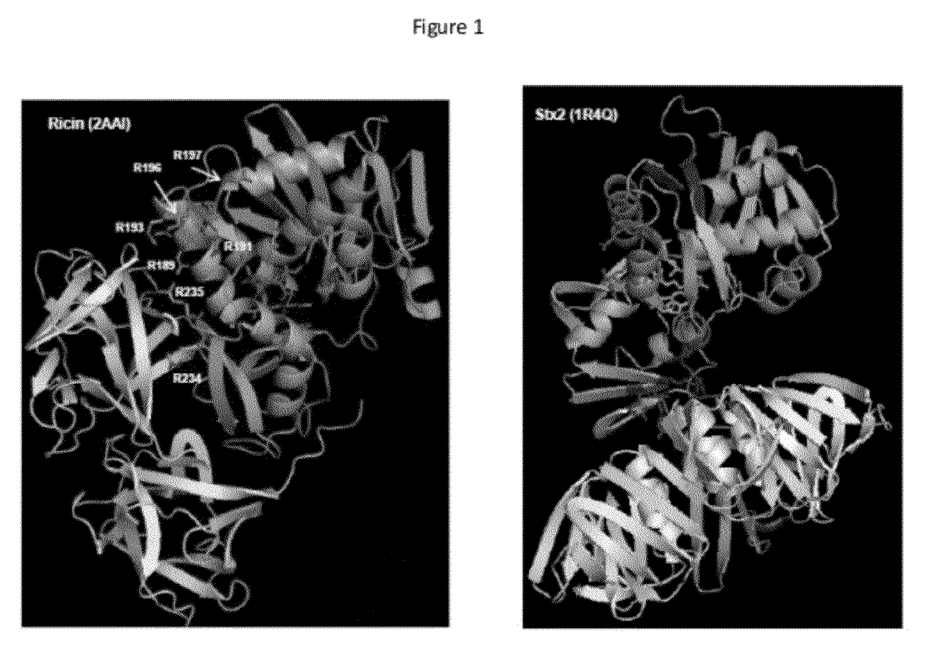
FIG. 1. Structure of ricin and Stx1. For ricin, RTA is in green and RTB is in yellow. Active site is red. The arginines that interact with ribosome in RTA are magenta. For Stx2, A1 is green, A2 is orange, the B pentamers are in yellow, active site is in cyan. The arginines that might interact with ribosome are in magenta and that might interact with rRNA are in red.
Figure 2:
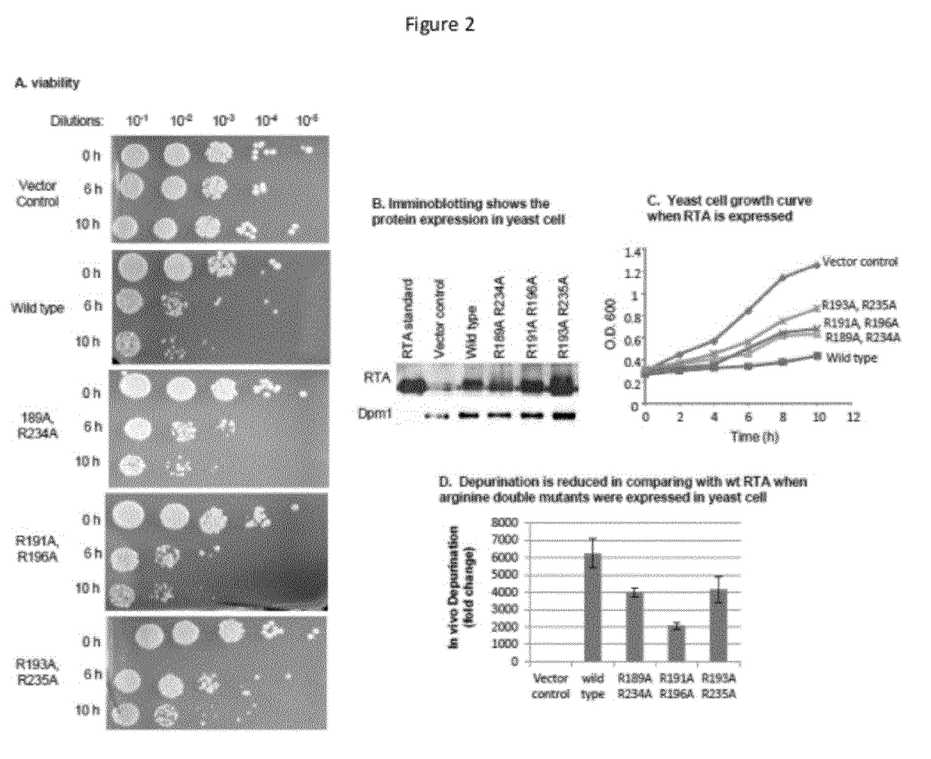
FIG. 2. Arginine double mutations reduce the depurination and cytotoxicity of RTA.

In our earlier studies, we showed that the C-terminal domain (CTD) of RTA, which interacts with the B subunit in the holotoxin, is near the ribosome binding site (7). In the x-ray crystal structure of the holotoxin, the B-chain (RTB) docks on the C-terminus of the A chain (RTA) and the arginine residues in RTA located at the interface are blocked by RTB (FIG. 1 shown in magenta). In Shiga toxin 2 (Stx2), the arginine residues that are predicted to interact with the rRNA are at the interface of the A and the B subunits (shown in red), while the arginine residues that are predicted to bind ribosomes are on the surface of the A subunit away from the active site (shown in magenta). To determine if the Arg residues at the interface of the A and B subunits are involved in ribosome binding, single mutations were introduced at R189A, R191A, R193A, R196A, R197A, R234A and R235A in RTA. In addition, double mutations were introduced at R189A/R234A, R191A/R196A and R193A/R235A. The growth rate and viability of each mutant was evaluated in yeast as previously described (6). The single mutations did not reduce cytotoxicity, whereas double mutations at R191A/R196A, R193A/R235A and R189A/R234A showed a reduction in toxicity and in growth rate (FIGS. 2A, B, C) compared to the wild type. Analysis of ribosome depurination in these mutants using the recently published quantitative reverse transcriptase polymerase chain reaction (qRT-PCR) method (12) indicated that depurination activity of these mutants was reduced in vivo (FIG. 2D).

Figure 3:
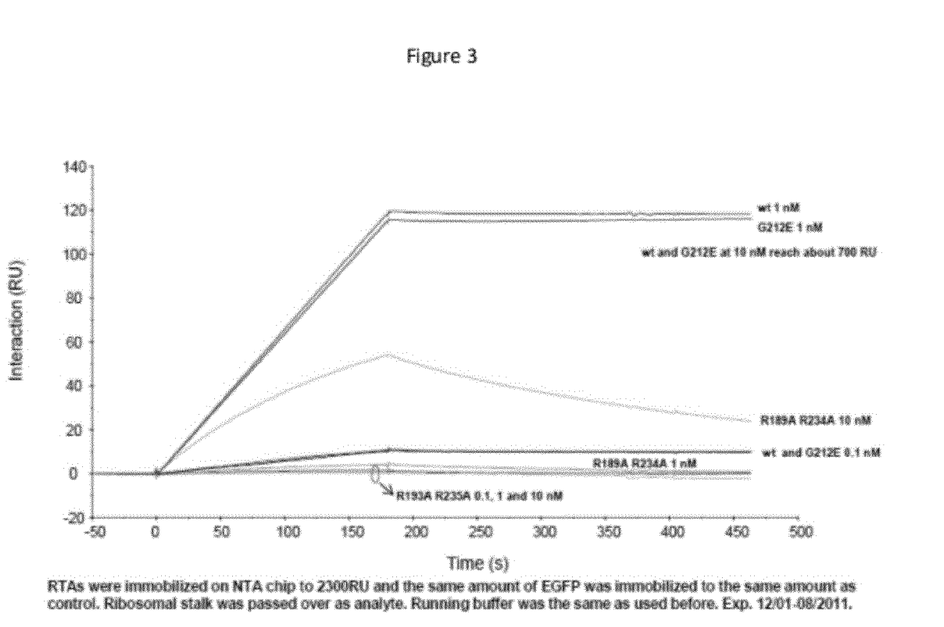
FIG. 3. R189A R234A double mutant has reduced interaction (less than 1/10), while R193A R235A double mutant has no interaction with the ribosomal stalk.

The R193A/R235A and R189A/R234A mutants were selected to study the interaction with ribosomes. The active site mutant, G212E, which had reduced toxicity and very low depurination activity (6) was used as a control. R193A/R235A, R189A/R234A and G212E were cloned into the E. coli expression plasmid, pET28 and N-terminal His-tagged recombinant protein was purified from E. coli. The interaction of each mutant with the isolated stalk pentamer from yeast was examined using surface plasmon resonance (SPR) with a Biacore instrument. The N-terminal His-tagged mutant was immobilized on the NTA chip and the isolated stalk pentamer was passed over the surface as the analyte. As shown in FIG. 3, the R189A/R234A mutant had very weak interaction with stalk complex, R193A/R235A mutant completely lost the interaction with the stalk complex, while the active site mutant, G212E was able to bind to the stalk.

Figure 4:
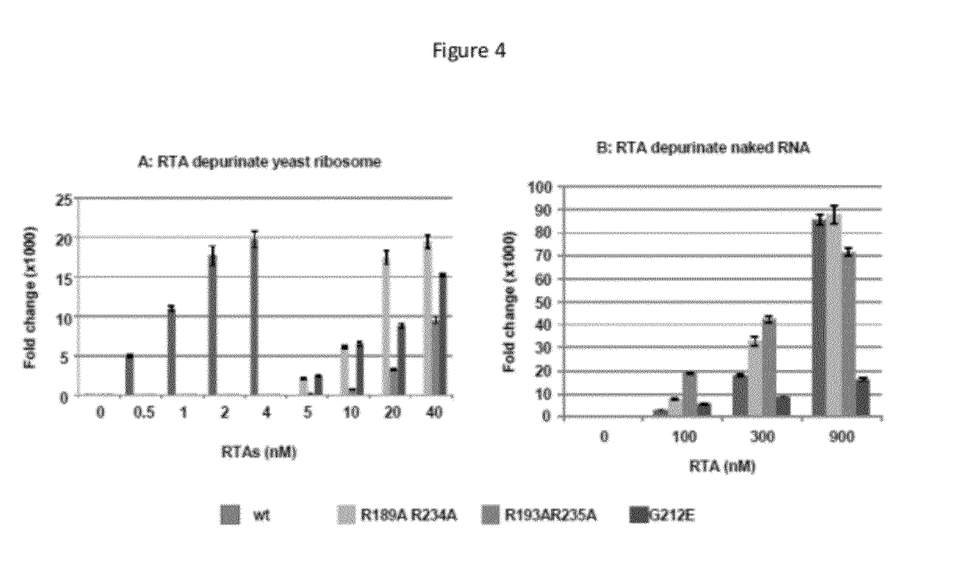
FIG. 4. R189A/R234A and R193A/R235A demonstrate comparable activity as wt RTA when naked rRNA was used as substrate but 20 to 40 times reduced activity when ribosomes were used as the substrate.

To determine if the arginine mutants are involved in ribosome binding, we examined the depurination activity of the three mutants using intact ribosomes or isolated rRNA lacking the ribosomal proteins as substrates. Our hypothesis was that if the ribosome binding site mutations disrupt ribosome binding, then these mutants should depurinate intact ribosomes at a reduced level compared to naked rRNA isolated from these ribosomes. In contrast, ribosome binding mutants should be able to depurinate the isolated rRNA at a similar level as the WT, since they contain an intact active site. As shown in FIG. 4, R189A/R234A, R193A/R235A and G212E depurinated yeast ribosomes at reduced rates of 15-, 40- and 20-fold compared to the WT RTA, respectively. However, when naked yeast 25S rRNA was used as the substrate, G212E had 3-fold reduced activity, while R189A/R234A and R193A/R235A depurinated the 25S rRNA at a similar rate as WT. Since R189A/R234A and R193A/R235A depurinated intact ribosomes less than WT, but depurinated the naked 25S rRNA at a similar rate as WT, we concluded that Arg 189, Arg 234, Arg193 and Arg235 were critical for binding to theribosome (or ribosomal stalk which is where RTA binds the ribosome), but not enzymatic activity. However, since additional interactions, outside of the interaction with the stalk, are observed between RTA and ribosomes (8), multiple mutations at Arg residues at the interface between the A and the B subunits are important for binding to other regions of the ribosome. We will combine the R193A/R235A mutation with the R189A/R234A mutation as indicated in Table 1. A double mutation in Arg213/Arg258 at the interface is predicted to bind rRNA (Table 1). Based on the similarity between the structure of RTA and Shiga toxin 2 shown in FIG. 1, we predict that Arg172, Arg 176 and Arg179 of the A subunit (shown in magenta) are likely to interact with the ribosome, while Arg 204, Arg219, Arg222, Arg247 and Arg250 in Shiga toxin 2 (shown in red) are predicted to interact with rRNA (Table 2). The corresponding residues in Stx1, Arg172, Arg176 and Arg179 are predicted to interact with ribosomes and Arg205, Arg220, Arg223, Arg248 and Arg251 are predicted to interact with the rRNA (Table 2).

TABLE 1

Arginines that affect ribosome or RNA binding of RTA
Ribosome Binding Mutation

R189A R234A
R193A R235A
R193A/R235A/R189A
R193A/R235A/R234A
R193A/R235A/R189A/R234A
R213A/R258A

TABLE 2

Arginines that affect ribosome
or RNA binding of Stx1 and Stx2
Ribosome Binding Mutation

| Stx1 | Stx2 |
| --- | --- |
| R172A/R176A/R179A | R172A/R176A/R179A |
| R205A/R220A | R204A/R219A |
| R223A/R248A | R222A/R247A |
| R251A | R250A |

As explained briefly above, site-directed mutagenesis was used to engineer these mutations into the mature forms of RTA or shigella toxin, which were transformed into yeast under a galactose inducible promoter. Cell viability was determined by plating dilutions of cells on glucose media after induction on galactose (6), and growth was measured with a BioTek Synergy 4 using the Kinetic Step Program that measures $OD_{600}$ every 30 min. Depurination activity was determined in yeast using the qRT-PCR assay with RNA isolated after induction and compared to the WT (12). Total translation was examined in vivo in yeast by [$^{35}$S]-methionine incorporation as previously described (10, 11).

To identify mutations that disrupt ribosome binding, we examined the interaction of the RTA mutants (RTA$^m$) with the isolated ribosomal stalk complex (8) and with intact ribosomes by SPR analysis. The use of yeast ribosomes to study biochemical interactions of RTA has been well established in our laboratory (2, 7, 8). RTA mutants were cloned into the E. coli expression plasmid, pET28 and N-terminal His-tagged recombinant protein was purified from E. coli. A Biacore T100 was used to analyze the interaction between ribosomes and WT or mutant forms of RTA using the protocols we established (2, 7). The N-His-tagged RTA was immobilized on the NTA chip as the ligand and the monomeric ribosomes were passed over the immobilized ligand as the analyte at different concentrations to monitor the dose dependence of the association and the dissociation and for kinetic analysis. The data was analyzed using the BIAevaluation software to determine the association ($k_{on}$) and the dissociation rate ($k_{off}$) and the equilibrium dissociation constant ($K_D$) (7, 8). As an alternative method, the interaction between the RTA′′′ and ribosomal stalk can also be studied by co-immunoprecipitation (co-IP) as previously described (8). RTA′′′ will be incubated with ribosomes or the stalk pentamer and antibodies against RTA will be used to co-IP the associated stalk proteins. Complexes will be resolved by SDS-PAGE and the stalk proteins will be detected by immunoblot analysis using monoclonal antibody to the conserved C-termini of the yeast and mammalian stalk proteins (14) as previously published (8).

Results

We examined the depurination activity of RTA′′′ in vitro using ribosomes and rRNA from yeast and rat liver as substrates. Depurination activity was examined by qRT-PCR using purified mutant proteins (12). Rates were determined in the linear range of concentration for each mutant in at least two independent experiments for ribosomes and rRNA. We have found that the conditions for depurination of ribosomes differ from the conditions for depurination of rRNA in vitro. Ribosomes will be depurinated using previously established conditions (12). The rRNA was depurinated in 20 mM citrate buffer pH 5.0 at 30° C., conditions we established experimentally as optimal for depurination of yeast rRNA by RTA. Similar optimization will be performed on rat liver ribosomes and rRNA for rate determinations. As controls, we used the active site mutant, G212E, which binds ribosomes like the WT, but causes very little depurination than the WT (FIGS. 3 and 4). As a complement to this approach, translation inhibitory activity of RTA′′′ will be examined in the cell-free rabbit reticulocyte lysate assay and the $IC_{50}$ values will be determined by constructing dose response curves (7).

Our results showed that ribosome binding site mutations that disrupt ribosome binding depurinate intact ribosomes at a reduced level compared to naked rRNA isolated from these ribosomes. Ribosome binding mutants depurinate the isolated rRNA at a similar level as the WT, since they contain an intact active site.

We will test the ability of RTA′′′ to induce cytotoxicity and apoptosis in MAC-T, HeLa and Vero cells, three cell lines that we have used in our studies of RTA toxicity (5).

Depurination levels will be determined by qRT-PCR assay (12) in cells exposed to recombinant WT-RTA and RTA′′′ for increasing time intervals between 1 to 6 h. Cytotoxicity will be examined by exposure of cells to WT-RTA and RTA′′′ using CellTiterGlo reagent (Promega) as described (13). Cell viability will be determined after 72 h of toxin exposure in serum-containing media. Apoptosis will be assessed using ELISA to measure caspase 3/7 activation, by western immunoblot of PARP analysis, and by the ROCHE cell death ELISA assay for apoptosome formation as described (5). Total translation will be determined by [$^{35}$S]-methionine incorporation as described (5). To assess activation of ribotoxic stress signaling cascades, cells will be treated with WT-RTA or RTA′′′ for increasing periods of time. Cell lysates will be collected as described in (5) and analyzed for JNK, p38 and ERK signaling by immunoblot analysis with antibodies that recognize phospho- and total forms of each protein.

These results indicate that ribosome binding mutants appear to exhibit reduced cytotoxicity than the active site mutants and thus should provide better vaccine candidates. These mutants might also be very useful in identifying epitopes on RTA that are recognized by antibodies that can neutralize or inhibit the activity of RTA.

These experiments will address the huge gap in our knowledge of how RIPs interact with mammalian ribosomes and how these interactions lead to ribosome depurination, translation inhibition, signaling and apoptosis.

REFERENCES

1. Bommer, U., N. Burkhardt, R. Junemann, C. M. T. Spahn, F. J. Triana-Alonso, and K. H. Nierhaus. 1996. Subcellular fractionation. In Graham, J. and Rickwoods. D. (eds)., A Practical Approach, IRL Press at Oxford University Press, Oxford:280-285.
2. Chiou, J. C., X. P. Li, M. Remacha, J. P. Ballesta, and N. E. Turner. 2008. The ribosomal stalk is required for ribosome binding, depurination of the rRNA and cytotoxicity of ricin A chain in Saccharomyces cerevisiae. Mol Microbiol 70:1441-52.
3. Garcia-Ortega, L., M. Masip, J. M. Mancheno, M. Onaderra, M. A. Lizarbe, M. F. Garcia-Mayoral, M. Bruix, A. Martinez del Pozo, and J. G. Gavilanes. 2002. Deletion of the NH2-terminal beta-hairpin of the ribotoxin alpha-sarcin produces a nontoxic but active ribonuclease. J Biol Chem 277:18632-9.
4. Gluck, A., and I. G. Wool. 1996. Determination of the 28 S ribosomal RNA identity element (G4319) for alpha-sarcin and the relationship of recognition to the selection of the catalytic site. J Mol Biol 256:838-48.
5. Jetzt, A. E., J. S. Cheng, N. E. Turner, and W. S. Cohick. 2009. Ricin A-chain requires c-Jun N-terminal kinase to induce apoptosis in nontransformed epithelial cells. Int J Biochem Cell Biol 41:2503-10.
6. Li, X. P., M. Baricevic, H. Saidasan, and N. E. Turner. 2007. Ribosome depurination is not sufficient for ricin-mediated cell death in Saccharomyces cerevisiae. Infect Immun 75:417-28.
7. Li, X. P., J. C. Chiou, M. Remacha, J. P. Ballesta, and N. E. Turner. 2009. A two-step binding model proposed for the electrostatic interactions of ricin a chain with ribosomes. Biochemistry 48:3853-63.
8. Li, X. P., P. Grela, D. Krokowski, M. Tchorzewski, and N. E. Turner. 2010. Pentameric organization of the ribosomal stalk accelerates recruitment of ricin a chain to the ribosome for depurination. J Biol Chem 285:41463-71.
9. Niwa, H., K. Yamamura, and J. Miyazaki. 1991. Efficient selection for high-expression transfectants with a novel eukaryotic vector. Gene 108:193-9.
10. Parikh, B. A., U. Baykal, R. Di, and N. E. Turner. 2005. Evidence for retro-translocation of pokeweed antiviral protein from endoplasmic reticulum into cytosol and separation of its activity on ribosomes from its activity on capped RNA. Biochemistry 44:2478-90.
11. Parikh, B. A., C. Coetzer, and N. E. Turner. 2002. Pokeweed antiviral protein regulates the stability of its own mRNA by a mechanism that requires depurination but can be separated from depurination of the alpha-sarcin/ricin loop of rRNA. J Biol Chem 277:41428-37.
12. Pierce, M., J. N. Kahn, J. Chiou, and N. E. Turner. 2011. Development of a quantitative RT-PCR assay to examine the kinetics of ribosome depurination by ribosome inactivating proteins using Saccharomyces cerevisiae as a model. RNA 17:201-10.
13. Saenz, J. B., T. A. Doggett, and D. B. Haslam. 2007. Identification and characterization of small molecules that inhibit intracellular toxin transport. Infect Immun 75:4552-61.
14. Vilella, M. D., M. Remacha, B. L. Ortiz, E. Mendez, and J. P. Ballesta. 1991. Characterization of the yeast acidic ribosomal phosphoproteins using monoclonal antibodies.

Proteins L44/L45 and L44' have different functional roles. Eur J Biochem 196:407-14.

15. Wales, R., P. T. Richardson, L. M. Roberts, H. R. Woodland, and J. M. Lord. 1991. Mutational analysis of the galactose binding ability of recombinant ricin B chain. J Biol Chem 266:19172-9.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A mutant ricin toxin that is mutated relative to the wild type ricin A chain toxin of SEQ ID NO: 1, wherein the mutations are selected from the group consisting of i) RI89A and R234A; ii) RI93A and R235A; iii) RI93A and R235A and RI89A; iv) RI93A and R235A and R234A; v) RI93A and R235A and RI89A and R234A; and vi) R213A and R258A.

2. The mutant ricin toxin claim 1, wherein the mutations are RI89A and R234A.

3. The mutant ricin toxin claim 1, wherein the mutations are RI93A and R235A.

4. The mutant ricin toxin claim 1, wherein the mutations are RI93A, R235A and RI89A.

5. The mutant ricin toxin claim 1, wherein the mutations are RI93A, R235A and R234A.

6. The mutant ricin toxin claim 1, wherein the mutations are RI93A, R235A, RI89A and R234A.

7. The mutant ricin toxin claim 1, wherein the mutations are R213A and R258A.

8. A composition comprising a mutant ricin toxin of claim 1 and a biologically acceptable carrier.

9. A method of eliciting an immune response to ricin A chain toxin, comprising administering to an animal at least one mutant ricin toxin of claim 1 in an amount effective to elicit an immune response to ricin A chain toxin.

* * * * *

SEQUENCE LISTING

```
<160> NUMBER OF SEQ ID NOS: 3

<210> SEQ ID NO 1
<211> LENGTH: 267
<212> TYPE: PRT
<213> ORGANISM: Ricinus communis

<400> SEQUENCE: 1

Ile Phe Pro Lys Gln Tyr Pro Ile Ile Asn Phe Thr Thr Ala Gly Ala
1               5                   10                  15

Thr Val Gln Ser Tyr Thr Asn Phe Ile Arg Ala Val Arg Gly Arg Leu
            20                  25                  30

Thr Thr Gly Ala Asp Val Arg His Glu Ile Pro Val Leu Pro Asn Arg
        35                  40                  45

Val Gly Leu Pro Ile Asn Gln Arg Phe Ile Leu Val Glu Leu Ser Asn
    50                  55                  60

His Ala Glu Leu Ser Val Thr Leu Ala Leu Asp Val Thr Asn Ala Tyr
65                  70                  75                  80

Val Val Gly Tyr Arg Ala Gly Asn Ser Ala Tyr Phe Phe His Pro Asp
                85                  90                  95

Asn Gln Glu Asp Ala Glu Ala Ile Thr His Leu Phe Thr Asp Val Gln
            100                 105                 110

Asn Arg Tyr Thr Phe Ala Phe Gly Gly Asn Tyr Asp Arg Leu Glu Gln
        115                 120                 125

Leu Ala Gly Asn Leu Arg Glu Asn Ile Glu Leu Gly Asn Gly Pro Leu
    130                 135                 140

Glu Glu Ala Ile Ser Ala Leu Tyr Tyr Tyr Ser Thr Gly Gly Thr Gln
145                 150                 155                 160

Leu Pro Thr Leu Ala Arg Ser Phe Ile Ile Cys Ile Gln Met Ile Ser
                165                 170                 175

Glu Ala Ala Arg Phe Gln Tyr Ile Glu Gly Glu Met Arg Thr Arg Ile
            180                 185                 190

Arg Tyr Asn Arg Arg Ser Ala Pro Asp Pro Ser Val Ile Thr Leu Glu
        195                 200                 205

Asn Ser Trp Gly Arg Leu Ser Thr Ala Ile Gln Glu Ser Asn Gln Gly
    210                 215                 220

Ala Phe Ala Ser Pro Ile Gln Leu Gln Arg Arg Asn Gly Ser Lys Phe
225                 230                 235                 240

Ser Val Tyr Asp Val Ser Ile Leu Ile Pro Ile Ile Ala Leu Met Val
                245                 250                 255

Tyr Arg Cys Ala Pro Pro Pro Ser Ser Gln Phe
            260                 265

<210> SEQ ID NO 2
<211> LENGTH: 251
<212> TYPE: PRT
<213> ORGANISM: Escherichia coli
<220> FEATURE:
<223> OTHER INFORMATION: Synthetic Sequence

<400> SEQUENCE: 2
```

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 3
<211> LENGTH: 250
<212> TYPE: PRT
<213> ORGANISM: Escherichia coli

<400> SEQUENCE: 3

Arg Glu Phe Thr Ile Asp Phe Ser Thr Gln Gln Ser Tyr Val Ser Ser
1               5                   10                  15

Leu Asn Ser Ile Arg Thr Glu Ile Ser Thr Pro Leu Glu His Ile Ser
            20                  25                  30

Gln Gly Thr Thr Ser Val Ser Val Ile Asn His Thr Pro Pro Gly Ser
        35                  40                  45

Tyr Phe Ala Val Asp Ile Arg Gly Leu Asp Val Tyr Gln Ala Arg Phe
    50                  55                  60

Asp His Leu Arg Leu Ile Ile Glu Gln Asn Asn Leu Tyr Val Ala Gly
65                  70                  75                  80

Phe Val Asn Thr Ala Thr Asn Thr Phe Tyr Arg Phe Ser Asp Phe Thr
                85                  90                  95

His Ile Ser Val Pro Gly Val Thr Val Ser Met Thr Thr Asp Ser
                100                 105                 110

Ser Tyr Thr Thr Leu Gln Arg Val Ala Ala Leu Glu Arg Ser Gly Met
            115                 120                 125
```

```
        Gln Ile Ser Arg His Ser Leu Val Ser Ser Tyr Leu Ala Leu Met Glu
            130                 135                 140

Phe Ser Gly Asn Thr Met Thr Arg Asp Ala Ser Arg Ala Val Leu Arg
        145                 150                 155                 160

Phe Val Thr Val Thr Ala Glu Ala Leu Arg Phe Arg Gln Ile Gln Arg
                        165                 170                 175

Glu Phe Arg Gln Ala Leu Ser Glu Thr Ala Pro Val Tyr Thr Met Thr
                    180                 185                 190

Pro Gly Asp Val Asp Leu Thr Leu Asn Trp Gly Arg Ile Ser Asn Val
                195                 200                 205

Leu Pro Glu Tyr Arg Gly Glu Asp Gly Val Arg Val Gly Arg Ile Ser
            210                 215                 220

Phe Asn Asn Ile Ser Ala Ile Leu Gly Thr Val Ala Val Ile Leu Asn
        225                 230                 235                 240

Cys His His Gln Gly Ala Arg Ser Val Arg
                        245                 250
```